US005763794A

United States Patent [19]
Marrelli

[11] Patent Number: 5,763,794
[45] Date of Patent: Jun. 9, 1998

[54] METHODS FOR OPTIMIZING SAMPLING OF A PETROLEUM PIPELINE

[75] Inventor: John David Marrelli, Houston, Tex.

[73] Assignee: Texaco Inc., White Plains, N.Y.

[21] Appl. No.: 790,035

[22] Filed: Jan. 28, 1997

[51] Int. Cl.⁶ .................................................. G01N 1/20
[52] U.S. Cl. .................. 73/863.02; 73/61.44; 364/554;
364/579; 324/640
[58] Field of Search ........................ 73/863.01, 863.02,
73/863.03, 863, 863.58, 863.81, 863.61,
61.44; 364/509, 554, 579; 324/640

[56] References Cited

U.S. PATENT DOCUMENTS

| | | | |
|---|---|---|---|
| 3,929,017 | 12/1975 | Kowelski | 73/863.02 X |
| 4,499,418 | 2/1985 | Helms et al. | 324/637 |
| 4,796,466 | 1/1989 | Farmer | 364/509 X |
| 4,827,430 | 5/1989 | Aid et al. | 364/510 |
| 4,947,127 | 8/1990 | Helms et al. | 324/640 |
| 5,001,434 | 3/1991 | Marrelli et al. | 324/640 |
| 5,067,356 | 11/1991 | Businger | 73/863.02 |
| 5,201,212 | 4/1993 | Williams | 364/509 X |
| 5,315,529 | 5/1994 | Farmer | 364/509 |
| 5,573,954 | 11/1996 | Greene et al. | 73/863 X |
| 5,621,180 | 4/1997 | Simon et al. | 73/863.01 X |

*Primary Examiner*—Thomas P. Noland
*Attorney, Agent, or Firm*—Henry H. Gibson; William J. Beard

[57] ABSTRACT

An isokinetic sampling method has been discovered for use in a pipeline carrying a three phase mixture of petroleum, water and gas. The method is used in combination with a fluid fraction measuring means capable of measuring physical characteristics indicative of fluid fraction. A statistically significant number of samples is analyzed over the range of sampler flow rate. The sampling flow rate is reset to correspond with the flow rate of the maximum standard deviation sample. As a result, samples most representative of the pipeline fluid fraction are withdrawn.

7 Claims, 1 Drawing Sheet

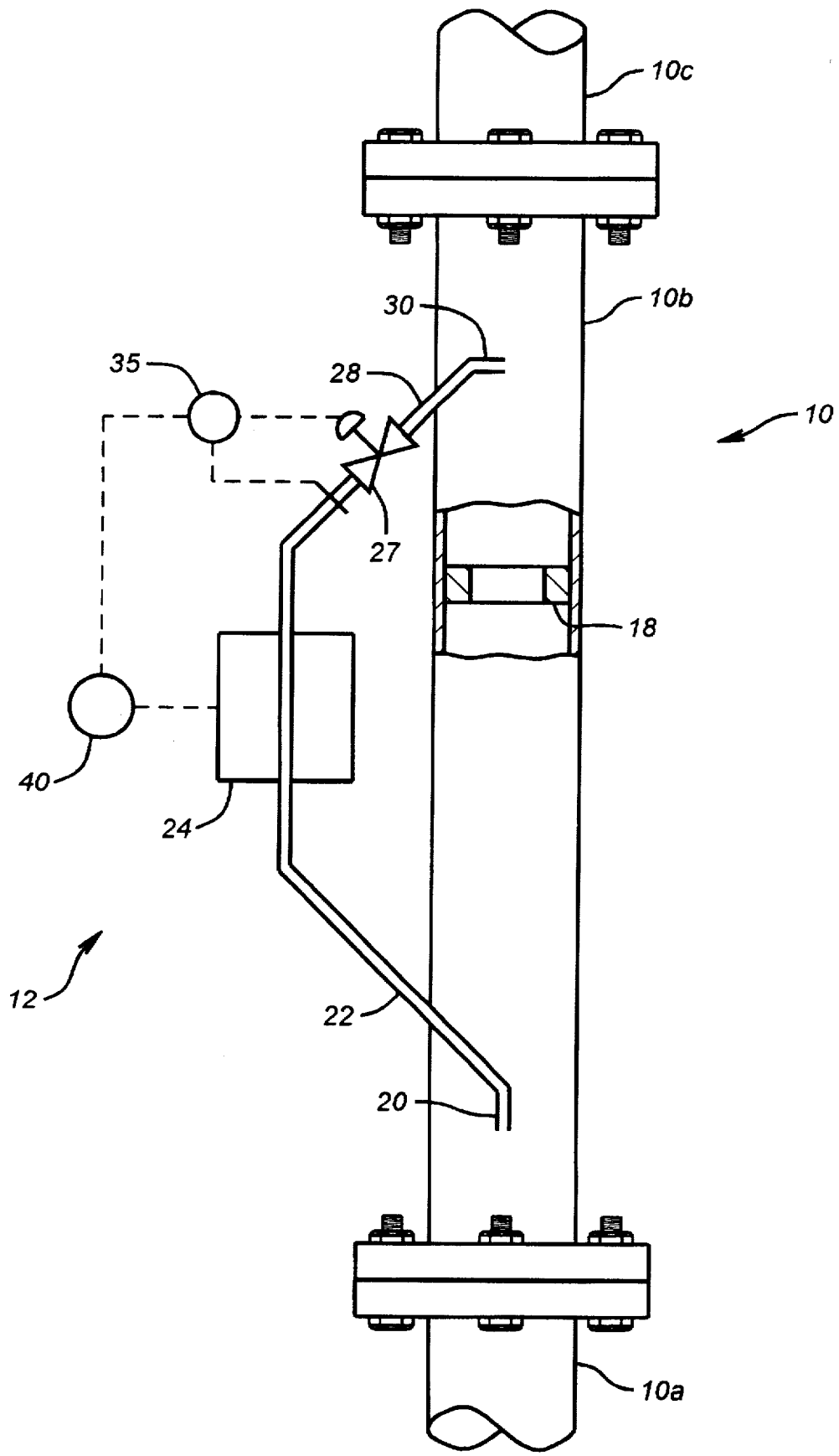

METHODS FOR OPTIMIZING SAMPLING OF A PETROLEUM PIPELINE

FIELD OF INVENTION

This invention relates to methods of sampling a pipeline carrying immiscible mixtures of water, petroleum and associated gas. The methods provide an optimum sample representative of the flowing mixture suitable for physical analysis.

BRIEF DESCRIPTION OF THE PRIOR ART

A watercut monitor is an instrument used in the petroleum industry to measure physical properties of aqueous petroleum mixtures. A source of microwave electromagnetic energy illuminates the flowing three phase stream of oil, water and gas and the relative phase shift and attenuation of transmitted and reflected microwave energy are sensed and measured. These measurements are interpreted in terms of this physical properties of the flowing stream, such as the relative proportions of oil, water, and gas and their volume flow rates.

It is known that the composition of a flowing multi-phase petroleum emulsion may actively fluctuate among petroleum continuous, water continuous and gas continuous modes. Such fluctuations can complicate or render erroneous measurements. The proportion of gas in a petroleum pipeline varies with changes in conditions such as pressure reduction along the pipeline. Another phenomenon causing difficulty in sampling a petroleum pipeline is the inertial separation of components according to density in the sample line and in the sample probe. Accordingly, there is a need in the art for an accurate method of taking a representative sample of a flowing three phase emulsion of water, gas and petroleum from a pipeline.

A watercut monitor instrument for composition analysis of a three phase petrolieum-water-gas sample is described in detail in co-assigned U.S. Pat. No. 4,499,418; U.S. Pat. No. 4,947,127 and U.S. Pat. No. 5,001,434. These patents are hereby incorporated by reference for all purposes.

BRIEF DESCRIPTION OF THE INVENTION

The invention comprises methods for sampling a multi-phase petroleum-water-gas fluid flowing through a pipeline under motive pressure. The sampling methods are used in conjunction with a multi-phase flow fluid fraction measuring means capable of measuring physical characteristics such as dielectric properties.

According to the methods of the invention a series of samples, typically a continuous series of samples, is withdrawn from the pipeline via a thin wall sampling apparatus such as a Pitot tube at a series of different flow rates. A statistically significant number of samples is taken for each flow rate over the flow range of the Pitot tube from a minimum sample flow rate to a maximum sample flow rate. Physical characteristics determinative of fluid fraction of each sample at each flow rate are measured to produce a series of measurements.

A standard deviation is calculated for the series of measurements. The sample series and corresponding flow rate having the highest standard deviation in the series is identified. Sample flow rate through the Pitot tube is then set to the rate at which the maximum standard deviation sample was taken.

Samples taken by the Pitot tube at maximum standard deviation are optimally representative of the multi-phase petroleum-water-gas fluid in the pipeline being measured.

BRIEF DESCRIPTION OF THE DRAWINGS

The single drawing is a schematic representation of an apparatus for carrying out the invention.

DETAILED DESCRIPTION OF THE INVENTION

Reference is made to the Drawing which is a schematic representation of a pipeline for transporting petroleum. The pipeline shown generally at 10 comprises an upstream portion 10a and a downstream portion 10c. Connecting upstream portion 10a and downstream portion 10c is a pipe segment 10b to which is attached a sampling and fluid fraction measuring means 12 such as a watercut monitor of the type previously referenced.

Sampling and fluid fraction measuring means 12 is envisioned to be a microwave measurement based instrument such as that described in U.S. Pat. No. 4,499,418; U.S. Pat. No. 4,947,127 and U.S. Pat. No. 5,001,434. Such an instrument is capable of measuring physical characteristics such as dielectric properties of attenuation of microwave energy or velocity of microwave propagation which are representative of droplet size and droplet density or number of droplets per unit volume in the 2 or 3 phase petroleum-water-gas mixture flowing through the pipeline.

It is known that errors in sampling three phase flow can produce fluid fraction measurements different from the actual composition in the pipeline. Reasons for these errors are due primarily to the difference in density and droplet size of the immiscible components and sample velocity. Sample velocities which are different from velocities in the pipeline may result in inertial separation of the sample resulting in distortion of the phase measurement.

Petroleum can have a density of 0.8 g/cm$^3$, water 1.0 g/cm$^3$ and associated gas 0.0001 g/cm$^3$ @ 1 atm. In easily measurable systems the immiscible components have similar densities. An example is heavy emulsified crude oil (1 g/cm$^3$) and fresh water (1 g/cm$^3$) with no gas present. A difficult example is light petroleum (0.6 g/cm$^3$), salty water (1.2 g/cm$^3$) with a varying amount of gas. This latter sample is particularly susceptible to inertial redistribution.

At the point of sampling, a change in velocity produces a redistribution of components based on density. Error is also attributable to changes in pressure and temperature and to surface active substances which influence size and shape of interphase surfaces. This inertial effect is particularly error prone when a thin wall sampling tube, such as a Pitot tube is used to capture the sample.

Flow restriction means such as an orifice plate 18 is fastened inside pipe segment 10b, intermediate between the ends thereof. A Pitot tube 20 is positioned upstream of orifice plate 18 and has an end open to direct flow in pipe segment 10b. A static tube 30 is positioned downstream of orifice plate 18 and has an end open to indirect (static) flow in pipe segment 10b. A first sample tube 22 is attached to and provides fluid communication between Pitot tube 20 and a test cell 24. A second sample tube 28 provides fluid communication between test cell 24 and static tube 30, via a control valve 27.

The purpose of the flow restrictions means, such as orifice plate 18, is to provide a pressure drop between Pitot tube 22 and static tube 28 so that a portion of the primary flow will pass through the fluid fraction measuring means 12. First and second sampling tubes 20,28 both have diameters much smaller than the diameter of pipe segment 10b. Both sampling tubes 20,28 may be provided with other valve means (not shown) to isolate the test cell 24.

The test cell 24 can be of known type such as that described in U.S. Pat. No. 4,499,418; U.S. Pat. No. 4,947,127 and U.S. Pat. No. 5,001,434 all incorporated herein by reference. The test cell 24 preferably provides a sample and includes a reference microwave source and microwave detectors. It is to be understood that this Drawing is extremely simplified and that many conventional details, such as the above mentioned isolation valves, have not been illustrated for the sake of simplicity in the Drawing and are understood by those skilled in the art and explained in more detail in the prior referenced patents.

Fluid fraction measuring means 12 extracts a small, continuous stream of the fluid from pipeline 10 upstream of orifice plate 18 and passes it through test cell 24. The sample in the test cell 24 is irradiated with microwave energy in the 10 gigahertz frequency region and the relative phase shift and attenuation of the microwaves traveling in both directions across the fluid are measured. These measurements may be made at varying rates up to several times per second. The sample then returns to pipeline 10, downstream of orifice plate 18. The velocity of the flow through test cell 24 is determined by the size and type of orifice plate 18 and the valve position of control valve 27. Closing valve 27 traps a sample of fluid in the test cell 24 of the measurement system 12. Opening and closing and controlling this valve 27 under feedback control based on the standard deviation of measurements made by the watercut monitor system 12 lies at the heart of the invention.

The position of control valve 27 may be varied under feedback control to best provide a sample representative of the fluid in pipeline 10. It has been discovered that the standard deviation of a physical measurement relating to the composition of the three phase mixture such as the relative phase shift or attenuation will be at a maxima at the point where the sampling rate is most representative of the fluid in the pipeline. This condition coincides with isokinetic flow.

Standard deviation is a statistical measure of the deviation from the average value of a data set. If the data is normally distributed (or Gaussian distributed) about 68% of the data set falls within one standard deviation of the average value. The kurtosis, or deviation from normality (the moment of the deviation about the average axis) is used to determine if the data is normally distributed (or Gaussian distributed) in a statistical sense. Low kurtosis indicates that the normality assumption is valid.

Change in phase composition of the flowing fluid causes large changes in the standard deviation of a physical measurement, but only a small change in the kurtosis or the average of the measurement. The standard deviation of the resulting data is described as the deviation of data around the average.

According to the invention, a series of samples at a given selected flow rate is withdrawn via Pitot tube 20 and first sample tube 22. The continuous series of samples is taken for several such selected flow rates over the full operating range of control valve 27 from maximum flow to minimum flow, e.g. 10% maximum. The samples are analyzed in test cell 24 by the measurement system 12 for a physical characteristic that is indicative of composition. Such physical characteristics may include droplet size, droplet density, microwave phase shift and microwave amplitude attenuation. The result is a series of measurements at each selected flow rate. The number of samples in the series must be sufficient to produce a statistically significant number of measurements. The standard deviation of the series of measurements at each selected flow rate is calculated in calculation and selection means 40. This may comprise, for example, a dedicated microprocessor such as an INTEL 80486 or the like and its internal memory. The highest standard deviation member in the series is identified. The sample flow rate is then reset under feedback control to the rate which produced the highest standard deviation member by means of flow rate controller 35. The controller 35 is simply a modem or interface between the microprocessor 40 and the analog valve 27. Thereby, samples are selected which are most representative of the three phase petroleum-water-gas mixture in the pipeline.

In the alternative, the function of calculation and selection means 40 and controller 35 may be carried out by hand. Likewise, the function of test cell 24 may be carried out at a laboratory bench.

While particular embodiments of the invention have been described, it will be understood that the invention is not limited thereto since many modifications can be made, and it is therefore, contemplated to cover by the appended claims any such modification as fall within the true spirit and scope of the invention.

What is claimed is:

1. In conjunction with a fluid fraction measuring means capable of measuring physical characteristics in a multi-phase petroleum-water-gas fluid flowing through a pipe under motive pressure, a method of controlling the sampling rate of the multi-phase petroleum-water-gas fluid entering a sample measurement system comprising the steps of:

withdrawing a series of flowing fluid samples by means of a thin wall sampling tube at each of a series of sample flow rates which are variable over a range from a minimum sample flow rate to a maximum sample flow rate, repetitively selecting a statistically significant number of fluid samples at each selected flow rate while varying the sample flow rate over the range and measuring a physical characteristic for each selected fluid sample at each flow rate to produce a series of physical characteristic measurements at each selected flow rate, calculating a standard deviation of each of the series of physical measurements at each flow rate and identifying the highest standard deviation in said series of physical measurements, adjusting the sample flow rate to that corresponding with the highest standard deviation sample, thereby withdrawing samples most optimally representative of the multi-phase petroleum-water-gas fluid in the pipe.

2. The method of claim 1 wherein the physical characteristic is attenuation of microwave energy.

3. The method of claim 1 wherein the physical characteristic is droplet size.

4. The method of claim 1 wherein the physical characteristic is droplet density or number of droplets per unit volume.

5. The method of claim 1 wherein the water includes inorganic salts.

6. The method of claim 1 wherein the thin wall sampling tube is a Pitot tube.

7. The method of claim 1 wherein more than one physical characteristic is measured.

\* \* \* \* \*